(12) United States Patent
Baird et al.

(10) Patent No.: US 12,185,937 B2
(45) Date of Patent: Jan. 7, 2025

(54) SYSTEMS AND METHODS FOR REPAIRING SOFT TISSUES USING NANOFIBER MATERIAL

(71) Applicant: CAYENNE MEDICAL, INC., Scottsdale, AZ (US)

(72) Inventors: Kevin N. Baird, Scottsdale, AZ (US); Derek J. Harper, Scottsdale, AZ (US); Kevin S. Nason, Chandler, AZ (US)

(73) Assignee: Cayenne Medical, Inc., Scottsdale, AZ (US)

( * ) Notice: Subject to any disclaimer, the term of this patent is extended or adjusted under 35 U.S.C. 154(b) by 0 days.

(21) Appl. No.: 18/234,626

(22) Filed: Aug. 16, 2023

(65) Prior Publication Data

US 2023/0389915 A1 Dec. 7, 2023

Related U.S. Application Data

(63) Continuation of application No. 17/565,425, filed on Dec. 29, 2021, now Pat. No. 11,759,198, which is a
(Continued)

(51) Int. Cl.
*A61B 17/04* (2006.01)
*A61B 17/00* (2006.01)

(52) U.S. Cl.
CPC ... *A61B 17/0401* (2013.01); *A61B 2017/00884* (2013.01); *A61B 2017/044* (2013.01);
(Continued)

(58) Field of Classification Search
CPC .... A61B 2017/00884; A61B 2017/044; A61B 2017/0445; A61F 2002/0829;
(Continued)

(56) References Cited

U.S. PATENT DOCUMENTS

| 5,578,057 A | 11/1996 | Wenstrom, Jr. |
| 6,123,711 A * | 9/2000 | Winters ............... A61B 17/68 606/304 |

(Continued)

FOREIGN PATENT DOCUMENTS

| CN | 107847253 A | 3/2018 |
| JP | 2007533371 A | 11/2007 |

(Continued)

OTHER PUBLICATIONS

U.S. Appl. No. 14/052,624 U.S. Pat. No. 9,901,334, filed Oct. 11, 2013, Systems and Methods for Repairing Soft Tissues Using Nanofiber Material.
(Continued)

*Primary Examiner* — Martin T Ton
(74) *Attorney, Agent, or Firm* — SCHWEGMAN LUNDBERG & WOESSNER, P.A.

(57) ABSTRACT

An anchoring system is a combination of a nanofiber scaffold material and an arthroscopically deployable suture anchor. The anchor is deployed into a bone tunnel using common techniques. The nanofiber material extends out of the proximal end of the implant, once deployed. The implant also includes pre-loaded sutures or has the ability to accept and lock sutures to the implant. For an implant pre-loaded with suture, the implant is placed into the bone, the material is deployed above the anchor onto the surface of the bone, suture is passed through the soft tissue, and knots are tied to secure the tissue against the bone, sandwiching the material between the bone and tissue, to provide a pathway for cells from the bone marrow to the soft tissue-bone interface, promote the healing response, provide a biomimetic structure that cells readily adhere to, and create a larger healing footprint.

20 Claims, 4 Drawing Sheets

Related U.S. Application Data continuation of application No. 16/815,507, filed on Mar. 11, 2020, now Pat. No. 11,534,155, which is a continuation of application No. 15/797,980, filed on Oct. 30, 2017, now Pat. No. 10,631,849, which is a continuation of application No. 14/052,624, filed on Oct. 11, 2013, now Pat. No. 9,901,334.

(60) Provisional application No. 61/713,230, filed on Oct. 12, 2012.

(52) U.S. Cl.
CPC ... *A61B 2017/0445* (2013.01); *A61L 2400/12* (2013.01); *A61L 2430/34* (2013.01)

(58) Field of Classification Search
CPC ........ A61F 2002/0864; A61F 2002/087; A61F 2002/0858; A61L 2400/12; A61L 2430/34
See application file for complete search history.

(56) References Cited

U.S. PATENT DOCUMENTS

| | | | |
|---|---|---|---|
| 6,280,474 B1* | 8/2001 | Cassidy | B29C 48/12 606/232 |
| 7,704,271 B2 | 4/2010 | Abdou | |
| 8,080,060 B2* | 12/2011 | Govil | A61F 2/28 623/23.61 |
| 8,795,334 B2 | 8/2014 | Astorino et al. | |
| 8,986,327 B2 | 3/2015 | Karasic et al. | |
| 9,173,645 B2 | 11/2015 | Overes et al. | |
| 9,320,512 B2 | 4/2016 | Dooney, Jr. | |
| 9,700,291 B2 | 7/2017 | Norton et al. | |
| 9,901,334 B2 | 2/2018 | Baird et al. | |
| 10,499,901 B2 | 12/2019 | Nason et al. | |
| 10,631,849 B2 | 4/2020 | Baird et al. | |
| 11,534,155 B2 | 12/2022 | Baird et al. | |
| 11,553,907 B2 | 1/2023 | Nason et al. | |
| 2006/0149266 A1* | 7/2006 | Cordasco | A61F 2/0811 606/76 |
| 2007/0010857 A1 | 1/2007 | Sugimoto et al. | |
| 2007/0255317 A1 | 11/2007 | Fanton et al. | |
| 2008/0154314 A1* | 6/2008 | McDevitt | A61F 2/447 623/13.14 |
| 2008/0188936 A1 | 8/2008 | Ball et al. | |
| 2008/0281325 A1* | 11/2008 | Stone | A61B 17/0401 606/60 |
| 2009/0062850 A1 | 3/2009 | Ken | |
| 2009/0306776 A1 | 12/2009 | Murray | |
| 2009/0317446 A1 | 12/2009 | Tan et al. | |
| 2010/0047309 A1 | 2/2010 | Lu et al. | |
| 2010/0292791 A1* | 11/2010 | Lu | A61P 37/06 623/13.12 |
| 2011/0028997 A1 | 2/2011 | Gregoire et al. | |
| 2011/0098727 A1 | 4/2011 | Kaiser et al. | |
| 2011/0264140 A1 | 10/2011 | Lizardi et al. | |
| 2011/0288566 A1 | 11/2011 | Kubiak | |
| 2012/0053622 A1 | 3/2012 | Schulman | |
| 2012/0101525 A1 | 4/2012 | Jenson et al. | |
| 2012/0158044 A1 | 6/2012 | Jenson et al. | |
| 2012/0211543 A1 | 8/2012 | Euteneuer | |
| 2012/0239085 A1 | 9/2012 | Schlotterback et al. | |
| 2013/0110165 A1 | 5/2013 | Burkhart et al. | |
| 2013/0123810 A1 | 5/2013 | Brown et al. | |
| 2014/0107700 A1 | 4/2014 | Baird et al. | |
| 2014/0257383 A1 | 9/2014 | Lombardo et al. | |
| 2014/0257385 A1 | 9/2014 | Lunn et al. | |
| 2014/0277133 A1 | 9/2014 | Foerster | |
| 2015/0173739 A1 | 6/2015 | Rodriguez et al. | |
| 2015/0250471 A1 | 9/2015 | Nason et al. | |
| 2016/0338688 A1 | 11/2016 | Nason et al. | |
| 2018/0042601 A1 | 2/2018 | Baird et al. | |
| 2020/0022695 A1 | 1/2020 | Nason et al. | |
| 2020/0205804 A1 | 7/2020 | Baird et al. | |
| 2022/0117596 A1 | 4/2022 | Baird et al. | |
| 2022/0117597 A1 | 4/2022 | Nason et al. | |

FOREIGN PATENT DOCUMENTS

| | | | |
|---|---|---|---|
| JP | 2011092742 A | | 5/2011 |
| JP | 2012052262 A | | 3/2012 |
| JP | 2014061379 A | | 4/2014 |
| JP | 2018520819 A | | 8/2018 |
| WO | WO-2006074550 A1 | | 7/2006 |
| WO | WO-2008100534 A2 | | 8/2008 |
| WO | WO-2013096224 A1 | | 6/2013 |

OTHER PUBLICATIONS

U.S. Appl. No. 15/797,980, U.S. Pat. No. 10,631,849, filed Oct. 30, 2017, Systems and Methods for Repairing Soft Tissues Using Nanofiber Material.
U.S. Appl. No. 16/815,507, U.S. Pat. No. 11,534,155, filed Mar. 11, 2020, Systems and Methods for Repairing Soft Tissues Using Nanofiber Material.
U.S. Appl. No. 17/565,425, filed Dec. 29, 2021, Systems and Methods for Repairing Soft Tissues Using Nanofiber Material.
U.S. Appl. No. 16/560,578 U.S. Pat. No. 11,553,907, filed Sep. 4, 2019, Systems and Methods for Repairing Soft Tissues.
U.S. Appl. No. 15/161,234 U.S. Pat. No. 10,499,901, filed May 21, 2016, Systems and Methods for Repairing Soft Tissues.
U.S. Appl. No. 17/565,428, filed Dec. 29, 2021, Systems and Methods for Repairing Soft Tissues.
"U.S. Appl. No. 14/052,624, Examiner Interview Summary mailed Jul. 6, 2017", 3 pgs.
"U.S. Appl. No. 14/052,624, Final Office Action mailed Mar. 29, 2017", 12 pgs.
"U.S. Appl. No. 14/052,624, Non Final Office Action mailed Jun. 15, 2017", 11 pgs.
"U.S. Appl. No. 14/052,624, Non Final Office Action mailed Sep. 7, 2016", 10 pgs.
"U.S. Appl. No. 14/052,624, Notice of Allowance mailed Oct. 12, 2017", 8 pgs.
"U.S. Appl. No. 14/052,624, Notice of Non-Compliant Amendment mailed Mar. 8, 2016", 2 pgs.
"U.S. Appl. No. 14/052,624, Notice of Non-Compliant Amendment mailed Apr. 14, 2016", 2 pgs.
"U.S. Appl. No. 14/052,624, Response filed Feb. 29, 2016 to Restriction Requirement mailed Aug. 31, 2015", 6 pgs.
"U.S. Appl. No. 14/052,624, Response filed May 22, 2017 to Final Office Action mailed Mar. 29, 2017", 8 pgs.
"U.S. Appl. No. 14/052,624, Response filed Jun. 14, 2016 to Notice of Non-Compliant Amendment mailed Apr. 14, 2016", 6 pgs.
"U.S. Appl. No. 14/052,624, Response filed Jun. 29, 2017 to Non Final Office Action mailed Jun. 15, 2017", 8 pgs.
"U.S. Appl. No. 14/052,624, Response filed Nov. 30, 2016 to Non Final Office Action mailed Sep. 7, 2016", 8 pgs.
"U.S. Appl. No. 14/052,624, Restriction Requirement mailed Aug. 31, 2015", 7 pgs.
"U.S. Appl. No. 15/161,234, Corrected Notice of Allowability mailed Oct. 30, 2019", 2 pgs.
"U.S. Appl. No. 15/161,234, Final Office Action mailed May 9, 2019", 13 pgs.
"U.S. Appl. No. 15/161,234, Non Final Office Action mailed Oct. 4, 2018", 12 pgs.
"U.S. Appl. No. 15/161,234, Notice of Allowance mailed Jul. 29, 2019", 8 pgs.
"U.S. Appl. No. 15/161,234, Preliminary Amendment filed Jun. 7, 2017", 7 pgs.
"U.S. Appl. No. 15/161,234, Response filed Jan. 4, 2019 to Non Final Office Action mailed Oct. 4, 2018", 11 pgs.
"U.S. Appl. No. 15/161,234, Response filed Jun. 19, 2019 to Final Office Action mailed May 9, 2019", 11 pgs.
"U.S. Appl. No. 15/797,980, Non Final Office Action mailed Sep. 5, 2019", 10 pgs.

(56) References Cited

OTHER PUBLICATIONS

"U.S. Appl. No. 15/797,980, Notice of Allowance mailed Dec. 27, 2019", 9 pgs.
"U.S. Appl. No. 15/797,980, Preliminary Amendment filed Oct. 31, 2017", 6 pgs.
"U.S. Appl. No. 15/797,980, Response filed Dec. 4, 2019 to Non Final Office Action mailed Sep. 5, 2019", 7 pgs.
"U.S. Appl. No. 16/560,578, Final Office Action mailed Aug. 30, 2022", 6 pgs.
"U.S. Appl. No. 16/560,578, Non Final Office Action mailed Jun. 8, 2022", 6 pgs.
"U.S. Appl. No. 16/560,578, Notice of Allowance mailed Sep. 30, 2022", 5 pgs.
"U.S. Appl. No. 16/560,578, Preliminary Amendment filed Sep. 9, 2019", 7 pgs.
"U.S. Appl. No. 16/560,578, Response filed Aug. 15, 2022 to Non Final Office Action mailed Jun. 8, 2022", 8 pgs.
"U.S. Appl. No. 16/560,578, Response filed Sep. 19, 2022 to Final Office Action mailed Aug. 30, 2022", 8 pgs.
"U.S. Appl. No. 16/815,507, Notice of Allowance mailed Aug. 22, 2022", 11 pgs.
"U.S. Appl. No. 16/815,507, Preliminary Amendment filed Mar. 12, 2020", 6 pgs.
"U.S. Appl. No. 17/565,425, Notice of Allowance mailed May 17, 2023", 14 pgs.
"U.S. Appl. No. 17/565,425, Preliminary Amendment filed Jan. 24, 2022", 5 pgs.
"U.S. Appl. No. 17/565,428, Preliminary Amendment filed Jan. 20, 2022", 6 pgs.
"Australian Application Serial No. 2013328971, First Examiners Report mailed Jun. 16, 2016", 3 pgs.
"Australian Application Serial No. 2013328971, Response filed Dec. 16, 2016 to First Examiners Report mailed Jun. 16, 2016", 22 pgs.
"Australian Application Serial No. 2016268130, First Examination Report mailed Aug. 22, 2019", 2 pgs.
"Australian Application Serial No. 2016268130, Response filed Sep. 6, 2019 to First Examination Report mailed Aug. 22, 2019", 1 pg.
"Australian Application Serial No. 2017202516, First Examination Report mailed Mar. 26, 2018", 3 pgs.
"Australian Application Serial No. 2017202516, Response filed Apr. 29, 2018 to First Examination Report mailed Mar. 26, 2018", 10 pgs.
"European Application Serial No. 13845008.5, Extended European Search Report mailed Mar. 23, 2017", 4 pgs.
"European Application Serial No. 13845008.5, Extended European Search Report mailed May 17, 2016", 8 pgs.
"European Application Serial No. 13845008.5, Response filed Jun. 12, 2017 to Communication pursuant to Article 94(3) EPC mailed Mar. 23, 2017", 6 pgs.
"European Application Serial No. 13845008.5, Response filed Nov. 20, 2015 to Communication pursuant to Rules 161(1) and 162 EPC mailed May 27, 2015", 6 pgs.
"European Application Serial No. 13845008.5, Response filed Nov. 29, 2016 to Extended European Search Report mailed May 17, 2016", 27 pgs.
"European Application Serial No. 16800570.0, Communication Pursuant to Article 94(3) EPC mailed Aug. 2, 2022", 5 pgs.
"European Application Serial No. 16800570.0, Extended European Search Report mailed Jan. 22, 2019", 10 pgs.
"European Application Serial No. 16800570.0, Response Filed Aug. 19, 2019 Extended European Search Report mailed Jan. 22, 2019", 8 pgs.
"European Application Serial No. 16800570.0, Response filed Aug. 20, 2018 to Office Action mailed Feb. 8, 2018", 9 pgs.
"European Application Serial No. 16800570.0, Response filed Dec. 12, 2022 to Communication Pursuant to Article 94(3) EPC mailed Aug. 2, 2022", 19 pgs.
"European Application Serial No. 18156124.2, Extended European Search Report mailed May 8, 2018", 6 pgs.
"European Application Serial No. 18156124.2, Response Filed Dec. 20, 2018 to Extended European Search Report mailed May 8, 2018", 22 pgs.
"International Application Serial No. PCT/US2013/064706, International Search Report mailed Mar. 10, 2014", 4 pgs.
"International Application Serial No. PCT/US2013/064706, Written Opinion mailed Mar. 10, 2014", 6 pgs.
"International Application Serial No. PCT/US2016/033680, International Preliminary Report on Patentability mailed Dec. 7, 2017", 8 pgs.
"International Application Serial No. PCT/US2016/033680, International Search Report mailed Sep. 12, 2016", 5 pgs.
"International Application Serial No. PCT/US2016/033680, Written Opinion mailed Sep. 12, 2016", 6 pgs.
"Japanese Application Serial No. 2015-536971, Office Action mailed Aug. 8, 2017", w/English Translation, 6 pgs.
"Japanese Application Serial No. 2015-536971, Response filed Oct. 20, 2017 to Office Action mailed Aug. 8, 2017", w/English Translation and English Claims, 10 pgs.
"Japanese Application Serial No. 2018-512839, Notification of Reasons for Refusal mailed Mar. 24, 2020", (W/ English Translation), 8 pgs.
"Japanese Application Serial No. 2018-512839, Response filed Jun. 12, 2020 to Notification of Reasons for Refusal mailed Mar. 24, 2020", (W/ English Translation), 19 pgs.
Inui, et al., "Regeneration of Rotator Cuff Tear Using Electrospun Poly (D,L-Lactide-Co- Clycolide) Scaffolds in a Rabbit Model", Arthroscopy: The Journal of Arthroscopic and Related Surgery, (Dec. 2012), 1790-1799.

* cited by examiner

SYSTEMS AND METHODS FOR REPAIRING SOFT TISSUES USING NANOFIBER MATERIAL

This application claims the benefit under 35 U.S.C. 119(e) of the filing date of Provisional U.S. Application Ser. No. 61/713,230, entitled Systems and Methods for Repairing Soft Tissues Using Nanofiber Material, filed on Oct. 12, 2012, which application is herein expressly incorporated by reference, in its entirety.

BACKGROUND OF THE INVENTION

Rotator cuff repair is the most common surgical repair performed in the shoulder, with more than 270,000 repairs performed annually in the United States, as of 2006, with that number expected to increase annually with concurrent increase in the aging population. Advances in rotator cuff repair technique have focused principally on transition from open repair, to mini-open repair, and more recently to fully arthroscopic repair. Moreover, advances have been made in suture patterns or arthroscopic repairs to better recreate the natural footprint insertion of the rotator cuff to improve time-zero mechanical properties, and in hopes of improving the healing rates.

In spite of improvements in surgical technique, healing rates as evidenced by postoperative ultrasound or MRI have varied widely, ranging from 91% healing rates in small tears to healing rates of only 10% in the largest tears. It is believed that healing rates are low due to the inadequate re-creation of the natural anatomic bone-tendon interface.

Various techniques have been employed to improve interface healing, including mesenchymal stem cells, xenograft, allograft, and acellular nanofiber scaffolds. Advances in nanofiber technology may hold promise in improving the bone-tissue interface healing of many soft tissue injuries, and have several advantages over other proposed methods. Issues of procurement, scalability, ease of use, and integration with currently performed surgical repair methods favor the nanofiber scaffolds. As noted in Inui et al. ("Regeneration of Rotator Cuff Tear Using Electrospun Poly (D,L-Lactide-Co-Glycolide) Scaffolds in a Rabbit Model"), *The Journal of Arthroscopic and Related Surgery*, Vol. 28, No. 12 (December), 2012: pp. 1790-1799, nanofiber size can range up to about 14 µm in the orthopedic field.

Usage of acellular augmentation devices have been evaluated in animal models, demonstrating safety to the animal and effectiveness in improving the soft tissue healing. Yokoya et al. ("Tendon-Bone Insertion Repair and Regeneration Using Polyglycolic Acid Sheet in the Rabbit Rotator Cuff Injury Model", *American Journal of Sports Medicine*, Vol. 36, no. 7, pp 1298-1309, 2008) used a polyglycolic acid (PGA) sheet to augment rotator cuff repairs of infraspinatus tendons in Japanese white rabbits, showing histological improvement in fibrocartilage layering and a slight improvement in tensile strength when compared to control tendons. Funakoshi et al. ("Rotator Cuff Regeneration Using Chitin Fabric as an Acellular Matrix", *Journal of Shoulder and Elbow Surgery*, Vol. 15, No. 1, pp. 112-118, 2006) demonstrated increased fibroblast presence and collagen formation when synthetic extracellular matrix was surgically applied to rotator cuff tears in Japanese white rabbits. MacGillivray et al. ("Biomechanical Evaluation of a Rotator Cuff Defect Model Augmented with a Bioresorbable Scaffold in Goats", *Journal of Shoulder and Elbow Surgery*, Vol. 15, No. 5, pp. 639-644, 2006) used polylactic acid patches in goats, showing safety to the animal but minimal difference between the treated and control groups. A similar experiment using a woven poly-L-lactide device was performed by Derwin et al. ("Rotator Cuff Repair Augmentation in a Canine Model with Use of a Woven Poly-L-Lactide Device", *Journal of Bone and Joint Surgery A*, Vol. 91, No. 5, pp. 1159-1171, 2009) in a dog model. A portion of each infraspinatus tendon was removed from the rotator cuff and then repaired in both shoulders. In one shoulder, a woven poly-L-lactide device was placed over the repair. In the other shoulder, the repair was left unaugmented. The augmented rotator cuff repair resulted in fewer tendon retractions, greater strength, and increased stiffness when compared to the contralateral untreated rotator cuff repairs.

In an attempt to improve the healing of the tissue-bone interface, acellular nanofiber scaffolds have been studied. Nanofiber scaffolds are typically made from materials with well-known biologic properties. For example, poly-lactide-co-glycolide (PLGA) is a material commonly used in absorbable sutures and medical devices. PLGA can be fashioned via electrospinning into nanofiber sheets, which in turn can be interposed between a torn tendon and the underlying bone attachment site during surgical tissue repair. Additionally, other polymers that are non-absorbable have been used as nanofiber scaffolds as well. When used in this manner it should be noted that the nanofiber is not acting as a structural graft under tension. The interposed fibers are used only as a scaffold to support ingrowth of host cells.

Moffat et al ("Novel Nanofiber-Based Scaffold for Rotator Cuff Repair and Augmentation", *Tissue Eng Part A*, Vol. 14, pp. 1-12, 2008) used an in vivo model to study the potential for an aligned nanofiber sheet to promote fibroblast formation and improved mechanical properties. They found that "mechanical properties of the aligned nanofiber scaffolds were significantly higher than those of the unaligned, and although the scaffolds degraded in vitro, physiologically relevant mechanical properties were maintained. These observations demonstrate the potential of the PLGA nanofiber-based scaffold system for functional rotator cuff repair. Moreover, nanofiber organization has a profound effect on cellular response and matrix properties, and it is a critical parameter for scaffold design." Some controversy exists over the best nanofiber architecture: monophasic, biphasic, or even triphasic.

Implantation of sheets of material as studied by Moffat, Derwin, MacGillivray, Funakoshi, and others requires an open surgical procedure. The current standard-of-care for rotator cuff repair is an arthroscopic procedure, growing from less than ten percent of all rotator cuff repairs in 1996 to almost sixty percent of all rotator cuff repairs in 2006. The trend has continued in the past 6 years, with current estimates suggesting that greater than 85% of rotator cuff repairs are performed arthroscopically. Further improvements to the procedure that are potentially offered by devices and/or materials as described by Moffat must be compatible with arthroscopic implantation methods in order to be widely accepted.

Rotator cuff repair surgery has evolved from predominately being performed with an open procedure to an arthroscopic procedure during the past 15 years. The current state-of-the art arthroscopic procedure generally utilizes one of the following approaches:
   a) as shown in FIG. 1, a single row of suture anchors 1 lying underneath the rotator cuff tendon 2 with sutures passed up through the tendon and securely tied to anchor the tendon to the bone 3;
   b) as shown in FIG. 2, a double row of suture anchors 1 lying underneath the rotator cuff tendon 2 with sutures passed up through the tendon and securely tied to anchor the tendon to the bone;

c) as shown in FIG. 3, a single row of suture anchors 1 lying underneath the rotator cuff tendon 2 with sutures passed up through the tendon, securely tied, with suture from knots extending laterally over the tendon and secured to the bone 3 with a knotless suture anchor 4 that is outside the margin of the tendon.

There are no prospective, randomized published studies that show a difference in outcome between the three procedure groups listed above and depicted in FIGS. 1-3, and in spite of improvements in surgical technique, failure rates (defined as the tendon not healing to the bone) as evidenced by postoperative ultrasound or MRI have varied widely, range from 9% in small tears, to 90% in the largest tears. It is believed that failure to heal is due to the inadequate re-creation of the natural anatomic bone-tendon interface.

Various techniques have been employed to improve interface healing, including mesenchymal stem cells, xenografts, allografts, and acellular nanofiber scaffolds. Advances in nanofiber technology may hold promise in improving the bone-tissue interface healing of many soft tissue injuries, and have several advantages over other proposed methods. Issues of procurement, scalability, ease of use, and integration with currently performed surgical repair methods favor the nanofiber scaffolds.

A product that combines the current arthroscopically-placed suture anchor implants with a nanofiber scaffold, as disclosed and described herein, will allow the surgeon to repair the rotator cuff using current arthroscopic methods.

SUMMARY OF THE INVENTION

As noted above, this invention is a combination of a nanofiber scaffold material and an arthroscopically deployable suture anchor and is intended to improve soft tissue-to-bone repair. The suture anchor is deployed into a bone tunnel using common arthroscopic surgical techniques. The nanofiber material extends from a location within the bone tunnel, out of the proximal end of the implant, to a portion of the material external to the bone surface, once deployed. The implant also includes pre-loaded sutures or has the ability to accept and lock sutures to the implant. For an implant pre-loaded with suture, the implant is placed into the bone, the material is deployed above the anchor onto the surface of the bone, suture is passed through the soft tissue, and knots are tied to secure the tissue against the bone, sandwiching the material between the bone and tissue. The suture anchor with nanofiber material improves the current repair in at least the following ways:

a) the material in the inventive system provides a pathway for cells from the bone marrow to the soft tissue-bone interface, accelerating and promoting the healing response;

b) the inventive system provides a biomimetic structure that cells readily adhere to; and c) the inventive system creates a larger healing footprint than with a suture anchor alone.

More particularly, there is disclosed an anchoring system for securing soft tissue to bone, which comprises an implant having a body for securement to bone and an insert comprising a nanofiber material attached to the implant body and having an extended surface for contacting the soft tissue. The implant further comprises external surface features, threads in the illustrated embodiments, for securing the implant within surrounding bone. The extended surface of the insert comprises a head formed of the nanofiber material, the nanofiber material being flexible so that the head is extendable from an undeployed retracted position to a deployed extended position.

The insert further comprises a portion extending distally from the head for securement to the anchor body. The insert distal portion comprises a tube of material and the head comprises a plurality of strips extending from a proximal end of the tube. The insert distal portion comprises the nanofiber material, which is mono-phasic in one embodiment.

In another aspect of the invention, there is disclosed an insert for use in a soft tissue anchoring system. The insert comprises an extended portion having an extended surface for engaging the soft tissue to be anchored, and a second portion for securing the extended portion to a bone anchor. The extended portion of the insert comprises a nanofiber material. The extended surface of the insert comprises a head formed of the nanofiber material, the nanofiber material being flexible so that the head is extendable from an undeployed retracted position to a deployed extended position for insertion into a procedural site. The second portion extends distally from the head for securement to a body of the bone anchor. The insert distal portion comprises a tube of material and the head comprises a plurality of strips extending from a proximal end of the tube. The insert second portion comprises the nanofiber material, wherein in one embodiment, the nanofiber material is mono-phasic.

In still another aspect of the invention, there is disclosed a method for securing soft tissue to bone, which comprises a step of inserting an implantable anchor having a body into a desired bone site, deploying a portion of a nanofiber insert secured to the anchor to an extended configuration, and approximating the soft tissue to the bone so that the soft tissue engages the extended portion of the nanofiber insert. The inserting step comprises placing the body of the implantable anchor into a bone tunnel and securing the body in place by engaging external features on the anchor body with adjacent bone. The approximating step comprises tensioning suture extending from the anchor body through the soft tissue to draw the soft tissue into close proximity with the bone, and then knotting free ends of the suture. The deploying step comprises removing a sheath constraining the nanofiber insert portion so that it expands to its extended configuration.

The invention, together with additional features and advantages thereof, may best be understood by reference to the following description taken in conjunction with the accompanying illustrative drawing.

DESCRIPTION OF THE PREFERRED EMBODIMENT

Referring now more particularly to FIGS. 4-7B, the inventive system and methods utilize nanofiber material which is incorporated into the suture anchor and deployed into the bone using standard arthroscopic surgical techniques. Once deployed, the material is located between the soft tissue and bone.

Figure 1:
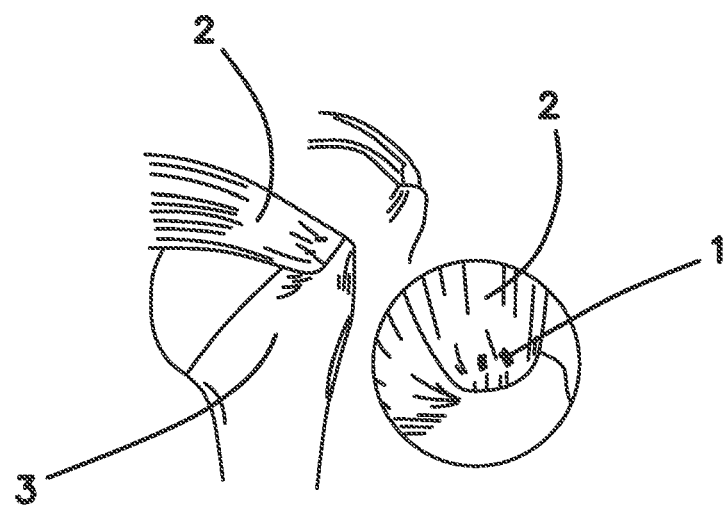
FIG. 1 is a schematic drawing of a first prior art approach for repairing a rotator cuff.
Figure 2:
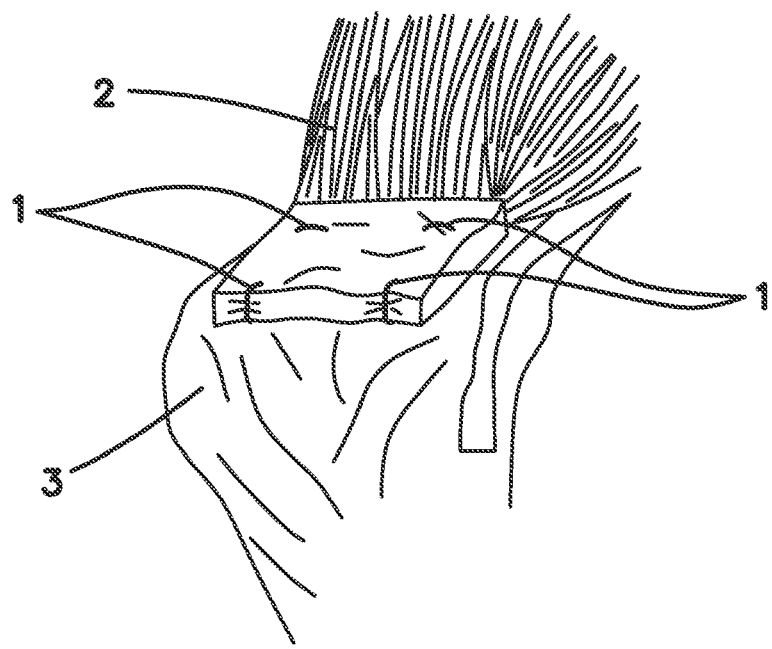
FIG. 2 is a schematic drawing of a second prior art approach for repairing a rotator cuff.
Figure 3:
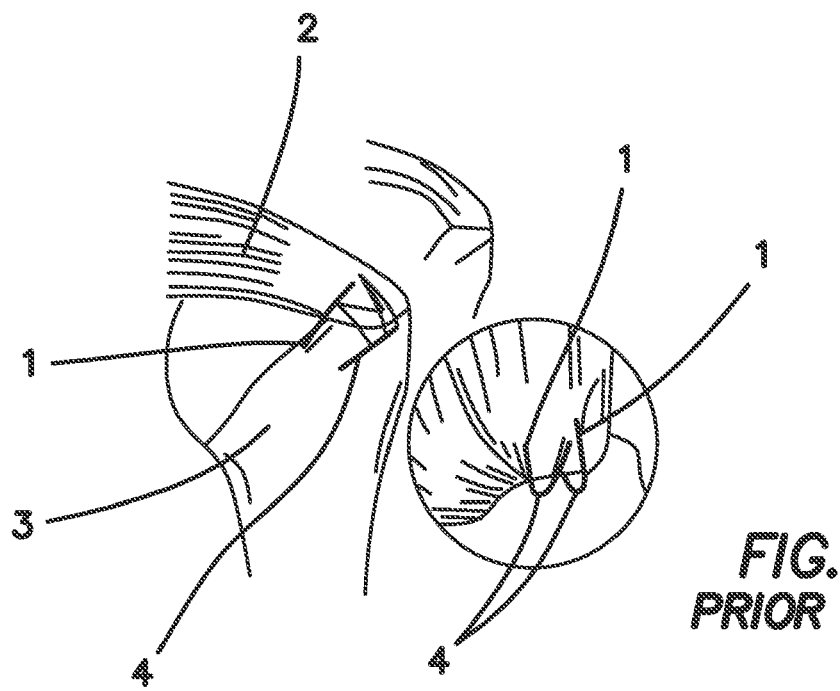
FIG. 3 is a schematic drawing of a third prior art approach for repairing a rotator cuff.
Figure 4:
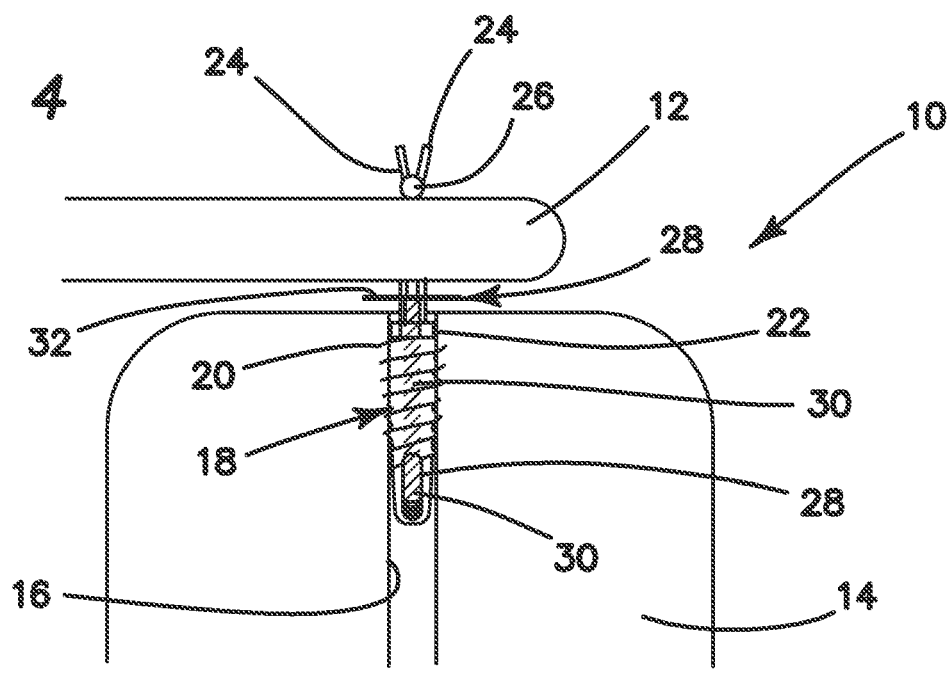
FIG. 4 is a schematic plan view of a system and method for repairing soft tissues in accordance with the principles of the present invention.
Figure 5:
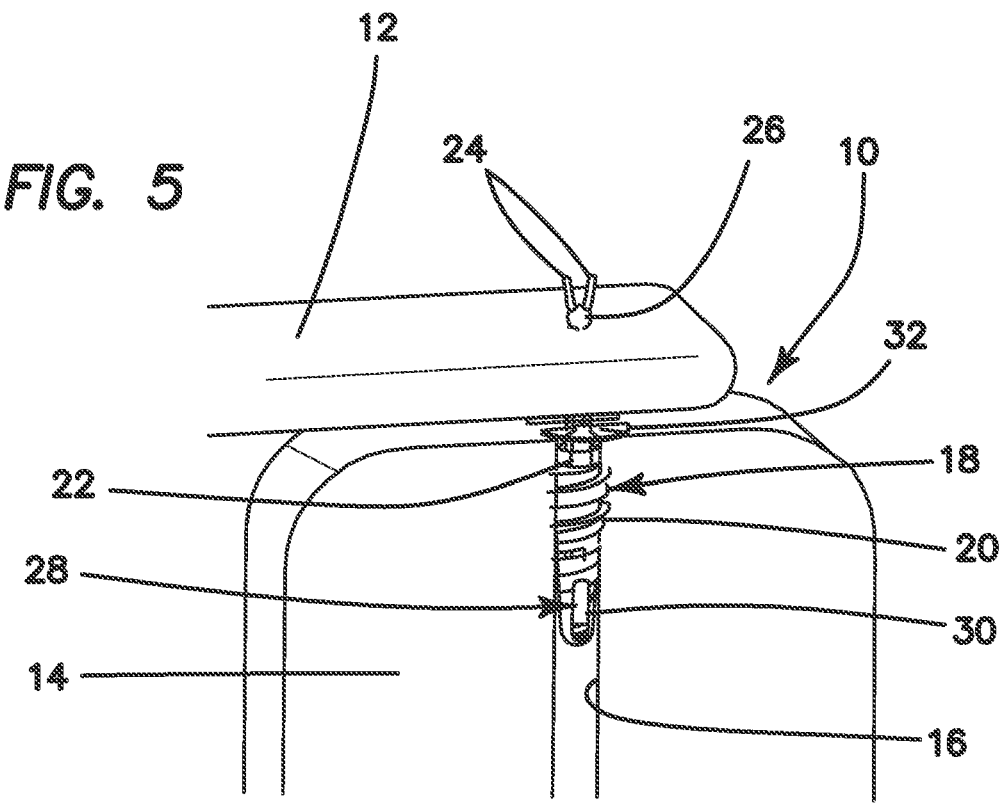
FIG. 5 is an isometric view of the system shown in FIG. 4.

FIGS. 4 and 5 illustrate the implementation of a soft tissue anchoring system 10 in accordance with the present invention. What is illustrated is a portion of soft tissue 12 which is to be attached to a portion of bone 14 using the anchoring system 10. The soft tissue 12 may comprise a rotator cuff tendon, to be secured to the humerus, as discussed above in conjunction with FIGS. 1-3, or the invention is equally applicable to any other site wherein attachment of soft tissue to bone is desired. A bone tunnel 16 is created in the bone 14 and a suture anchor 18 is placed within the bone tunnel 16, as shown, using common surgical techniques, which may or may not be arthroscopic. The illustrated suture anchor 18 comprises a hollow anchor body, having threads 20 or other suitable structure for engaging adjacent bone forming walls of the tunnel 16 to fix the anchor 18 in place within the tunnel. This type of corkscrew suture anchor is well known in the art. Other suitable types of suture anchors may also be employed. The suture anchor also has an eyelet 22 or other suitable structure for securing suture 24 to the anchor, which suture extends through the soft tissue 12 and secured thereto by means of a knot 26 or other suitable means. Thus, the soft tissue 12 is secured to the adjacent bone 14 by extending the free ends of the suture 24 through the soft tissue 12, securing the anchor 18 within the bone tunnel 16, tensioning the suture 24 until the soft tissue 12 is approximated to the adjacent bone 14, then creating the suture knot 26 to secure the soft tissue in place. This basic technique is well known in the art.

The present inventive system comprises a member or insert 28 which is comprised of a nanofiber material. More particularly, the nanofiber material is, in one embodiment, a monophasic nanofiber scaffold, which are known in the art, as described in the prior art references discussed in the Background portion of this application. Alternatively, a multi-phasic nanofiber scaffold, such as disclosed and described in U.S. Published Patent Application No. 2010/0292791 to Lu et al., herein expressly incorporated by reference in its entirety, may be used. The nanofiber scaffold member 28 extends into the bone tunnel 16 through the hollow center of the anchor 18, and expands outwardly at the bone surface to maximize surface area contact between the tissue and bone.

Material Configuration and Deployment

There are many configurations which the inventive nanofiber member 28 may assume. Two such alternative examples are illustrated in FIGS. 6A-6C and FIGS. 7A-7C, respectively. Each configuration shows the material in the deployed state. Prior to deployment of the anchor into the bone, the material is rolled in a cylindrical fashion around the implant inserter shaft and held in place (and protected) by a tubular sheath. This allows the use of traditional arthroscopic surgical techniques to place the implant into the bone. Once the implant is placed into the bone, the sheath is retracted and the nanofiber material is spread out to maximize the surface area contact between the tissue and bone.

Material Orientation

The nanofiber material can be manufactured with the fibers organized in a random orientation (unaligned) or aligned in one direction (aligned). There are three primary reasons why fiber alignment is important when coupled with the suture anchor.

a) As shown by Moffat, aligned fibers provide a pathway for faster cell growth and travel. One presently preferred configuration has a scaffold with fibers aligned axially within the anchor in the direction of cell travel from the bone marrow to the bone surface.

b) Fiber orientation can be controlled to mimic the tissue being repaired. For example, the rotator cuff (supraspinatus) has linearly oriented fibers. The scaffold material exposed to the supraspinatus may have aligned fibers in the same direction as the tissue, thus promoting faster and more complete tissue ingrowth. Markings on the inserter or anchor may facilitate proper alignment of the material to the tissue.

c) Fiber orientation determines the mechanical strength of the scaffold material. Aligned material has high tensile strength in the direction of the fibers and weak tensile strength in the direction perpendicular to the fibers. Unaligned material exhibits tensile strength in between that of aligned material pulled in two perpendicular directions. The material can be constructed and oriented in the anchor in such a way to increase the strength where necessary.

Material Attachment

There are several ways the material may be attached to an implant. For implants pre-loaded with suture, the material may be looped around the same eyelet as the suture or passed around a secondary eyelet. Another method for attachment is mechanically fastening the material to the anchor using a cleat, screw or post. The material may also be pinched between two halves of an implant. The material may be attached to a portion of an implant using a knot or adhesive. The material may also be bonded to the implant with the use of solvent.

As noted above, two exemplary embodiments of the present inventive system are illustrated in FIGS. 6A-6C and 7A-7C, respectively. In each embodiment, the nanofiber insert 28 comprises a distal portion or shaft 30 for attaching the insert 28 to the anchor 18, and a proximal head 32. As shown in FIGS. 4 and 5, the insert 28, when the suture anchor is deployed, is disposed so that the distal portion 30 extends through the suture anchor 18, as shown. A proximal end of the distal portion 30 extends proximally of the proximal end of the anchor body, and the head 32 is disposed at a proximal end of the insert distal portion, as shown.

Figure 7A:
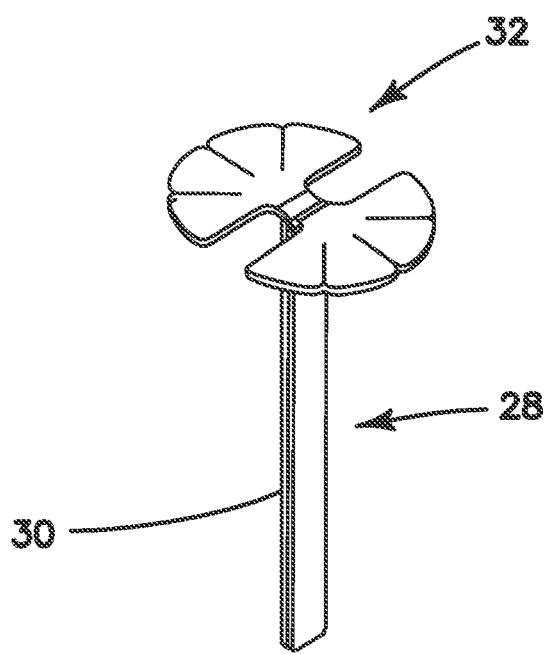
FIG. 7A is an isometric view of another embodiment of a nanofiber device according to the present invention.
Figure 7B:
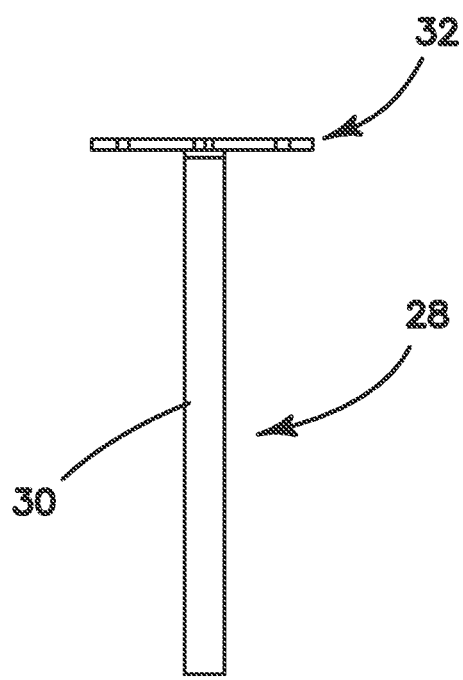
FIG. 7B is a plan view of the device of FIG. 7A.
Figure 6A:
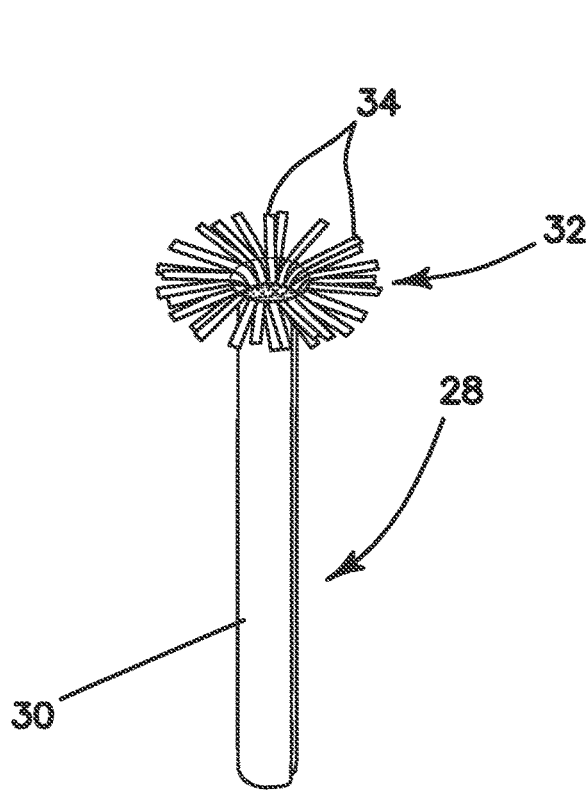
FIG. 6A is an isometric view of one embodiment of a nanofiber device according to the present invention.
Figure 6B:
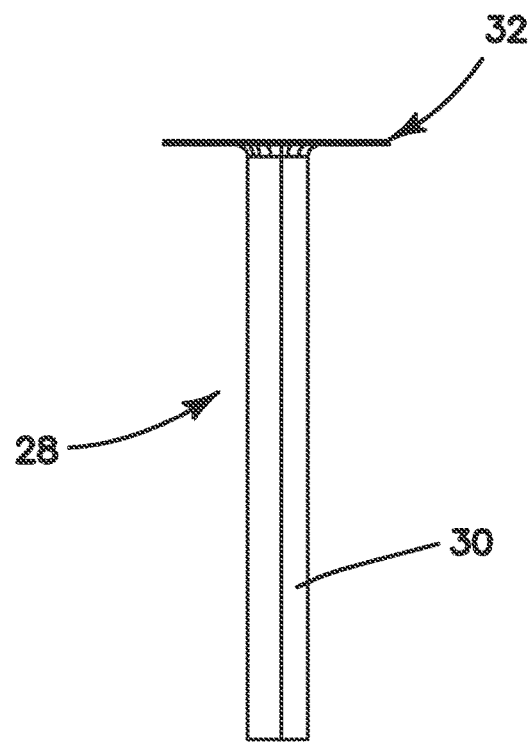
FIG. 6B is a plan view of the device of FIG. 6A.
Figure 6C:
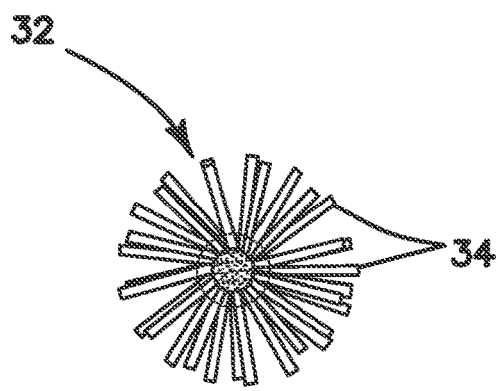
FIG. 6C is a top view of the device of FIGS. 6A and 6B.
Figure 7C:
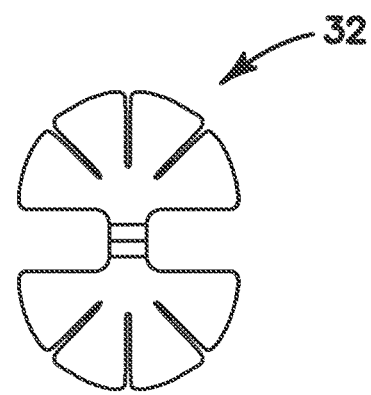
FIG. 7C is a top view of the device of FIGS. 7A and 7B.

FIGS. 6A-6C illustrates an embodiment wherein the insert distal portion 30 comprises a tube of material with strips 34 cut in the proximal end to allow the material to be deployed and spread out radially, as shown, to form the proximal head 32 and increase the surface contact between the tissue and bone. The tube comprises the distal portion 30 which is secured to the implant. FIGS. 7A-7C illustrates an alternative embodiment, wherein the insert 28 comprises a die-cut sheet material in the deployed condition. The long portions form the distal portion 30 which is disposed within the implant that is deployed into bone.

Additional Embodiments and Applications

An additional embodiment of the invention is an implant as previously described, with nanofiber material fixed solely to the proximal end (proximal defined as the end of the implant that is adjacent to the soft tissue, and distal defined as the end of the implant farthest in the bone). The nanofiber material covers just the surface area of the proximal end of the implant or possibly extends further proximally and/or radially away from the central axis of the implant.

Another additional embodiment of the invention is an implant as previously described, wherein the nanofiber material is fixed mechanically, with an adhesive, or by solvent bonding.

Yet another additional embodiment of the invention is an implant as previously described wherein the method of attachment of the material to the implant is via the use of a suture tether that is attached to the implant and the material. The material may be either fixed or movable. To enable the material to be moved into position, the suture is configured such that the surgeon pulls on the free end of the suture which moves the material closer to the implant, allowing the surgeon to position the material into a desired location. The position of the material relative to the implant is set prior to insertion of the implant into the bone or after the implant is deployed into the bone. Once the material is in position it is locked in place or reversibly movable. This may also be incorporated into two or more implants to allow the material to be placed in an adjustable location determined by the surgeon on the bone in between two or more implants.

Still another additional embodiment of the invention is an implant as previously described, wherein the nanofiber material is contained internal to the implant, along its central axis. The material extends at or near the distal tip and at, near or beyond the proximal end of the implant.

Another additional embodiment of the invention is an implant as previously described wherein the material may also be contained externally to the implant or within external channels.

Yet another additional embodiment of the invention is two or more implants as previously described with a bridge of nanofiber material strung between each implant. This configuration might best be described as a blanket of nanofiber material anchored at each implant, with the nanofiber material incorporated within or along the exterior of the implants.

Other applications of the invention include, but are not limited to, applications where soft tissue is re-attached surgically or arthroscopically to bone in locations such as knee, shoulder, foot, ankle, elbow, wrist, hand, spine, and hip. Surgical specialties that could utilize the invention include sports medicine, trauma, spine, foot and ankle, hand, hip, and extremities.

Moffat and others have shown that the use of nanofiber scaffolds promote cell attachment and growth in both aligned and unaligned orientations. The present invention improves the ease of use of nanofiber scaffolds for surgeons by pre-attaching the scaffold to a current, state-of-the-art suture anchor that can be implanted using standard arthroscopic procedures.

Arthroscopic surgeons do not want to complicate their surgical procedures. The value of nanofiber scaffolds in sheet form as proposed by Moffat will be substantially diminished due to the fact that surgeons will be reluctant to use a product that requires an open surgical procedure versus an arthroscopic procedure. The present invention facilitates arthroscopic use of nanofiber scaffolds, potentially increasing their value by several fold.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. A method of arthroscopic rotator cuff repair, comprising:
   delivering an anchor arthroscopically into a tunnel formed in a humerus through an opening in an outer surface of the humerus, wherein, during said delivering, the anchor has a flexible insert coupled thereto which includes a distal portion of the flexible insert extending into the anchor and a proximal head portion of the flexible insert remaining outside the anchor, the distal portion and the proximal head portion being formed from a single unitary piece of fiber material, wherein the distal portion extending into the anchor includes the distal portion having a plurality of fibers in axial alignment with a longitudinal axis of the anchor, wherein the anchor includes a distal opening in an exterior of the anchor proximate a leading end of the anchor such that, following said delivering, cells from bone marrow within the tunnel can travel into the anchor through the distal opening and in a proximal direction along the plurality of fibers of the distal portion toward the proximal head portion; and
   positioning the proximal head portion of the flexible insert over the humerus and under a rotator cuff tissue so that the proximal head portion is sandwiched between the humerus and the rotator cuff tissue in the form of a flexible sheet for promoting a healing response between the humerus and the rotator cuff tissue.

2. The method of claim 1 further comprising removing the proximal head portion from a delivery sheath.

3. The method of claim 2, wherein the proximal head portion is held in a constrained condition in the delivery sheath prior to said removing and can spread out from said constrained condition following said removing.

4. The method of claim 1, wherein the distal portion of the flexible insert extends to a location within the anchor proximate the leading end of the anchor.

5. The method of claim 1, wherein the distal portion of the flexible insert extends to the distal opening in the exterior of the anchor.

6. The method of claim 1, wherein the distal portion of the flexible insert extends through the anchor.

7. The method of claim 1, wherein said delivering leaves a suture coupled to the anchor and extending out of the tunnel.

8. The method of claim 7, wherein the suture is left extending through a delivery sheath.

9. The method of claim 7, wherein, prior to said delivering, the anchor is pre-loaded with the suture.

10. The method of claim 7 further comprising tensioning the suture following said positioning so as to approximate the rotator cuff tissue to the humerus.

11. The method of claim 7, wherein the flexible insert is movable along the suture.

12. A method of arthroscopic rotator cuff repair, comprising:
   anchoring a flexible insert in a tunnel formed in a humerus through an opening in an outer surface of the humerus, the flexible insert including a distal portion extending into the tunnel and a proximal head portion remaining outside the tunnel, the distal portion and the proximal head portion being formed from a single unitary piece of fiber material with the distal portion having a first width and the proximal head portion having a second width that is wider than said first width, wherein the distal portion extending into the tunnel includes the distal portion having a plurality of fibers in axial alignment with a longitudinal axis of the tunnel such that, following said anchoring, cells from bone marrow within the tunnel can travel along the plurality of fibers in a proximal direction so as to move along the distal portion toward the proximal head portion; and positioning the proximal head portion of the flexible insert over the humerus and under a rotator cuff tissue so that the proximal head portion is sandwiched between the humerus and the rotator cuff tissue in the form of a flexible sheet for promoting a healing response between the humerus and the rotator cuff tissue.

13. The method of claim 12, wherein said anchoring includes delivering an elongate anchoring member into the tunnel to anchor the flexible insert.

14. The method of claim 13, wherein the distal portion of the flexible insert extends through the elongate anchoring member.

15. The method of claim 13, wherein the distal portion of the flexible insert extends into a hollow interior portion of the elongate anchoring member.

16. The method of claim 15, wherein the distal portion of the flexible insert is visible from outside the elongate anchoring member through a distal opening in an exterior of the elongate anchoring member that is proximate a leading end of the elongate anchoring member.

17. The method of claim 12, wherein said delivering leaves a suture coupled to the elongate anchoring member and extending out of the tunnel.

18. The method of claim 17, wherein, prior to said delivering, the elongate anchoring member is pre-loaded with the suture.

19. The method of claim 12, wherein the distal portion of the flexible insert is in the form of a sheet.

20. The method of claim 12 further comprising removing the proximal head portion from a delivery sheath.

\* \* \* \* \*